United States Patent [19]
Descamps et al.

[11] Patent Number: 5,789,390
[45] Date of Patent: Aug. 4, 1998

[54] METHOD FOR PREPARING RECOMBINANT ADENO-ASSOCIATED VIRUSES (AAV), AND USES THEREOF

[75] Inventors: Vincent Descamps, Marly le Roi; Michel Perricaudet, Ecrosnes, both of France

[73] Assignee: Rhone-Poulenc Rorer S.A., Antony, France

[21] Appl. No.: 682,520

[22] PCT Filed: Jan. 18, 1995

[86] PCT No.: PCT/FR95/00054

§ 371 Date: Jul. 25, 1996

§ 102(e) Date: Jul. 25, 1996

[87] PCT Pub. No.: WO95/20671

PCT Pub. Date: Aug. 3, 1995

[30] Foreign Application Priority Data

Jan. 28, 1994 [FR] France ................... 94 00934

[51] Int. Cl.$^6$ .......... A61K 39/235; C12N 7/01; C12P 21/00; C07H 21/04
[52] U.S. Cl. .......... 514/44; 424/233.1; 424/199.1; 435/235.1; 435/69.1; 435/172.3; 536/23.5
[58] Field of Search .......... 435/235.1, 69.1, 435/172.3; 424/233.1, 199.1; 514/44; 536/23.5

[56] References Cited

U.S. PATENT DOCUMENTS 5,139,941  8/1992  Muzyczka et al. ........... 435/172.3
5,354,678  10/1994  Lebkowski et al. ........... 435/172.3

FOREIGN PATENT DOCUMENTS

0488528A1  6/1992  European Pat. Off.

WO91/18088  11/1991  WIPO.

OTHER PUBLICATIONS

Report and Recommendations of the Panel to Assess the NIH Investment in Research on Gene Therapy, Dec. 7, 1995
Coglan, New Scientist, 25 Nov. 1995, pp. 14–15.
Spibey et al. J Gen Virol, vol. 70, 1989, pp. 165–172.
Cukor et al., Biology of Adeno–Associated Virus, The Parvoviruses, Plenum 33–66 (1984).
Hermonat et al., Use of adeno–associated virus as a mammalian DNA cloning vector: Transduction of neomycin resistance into mammalian tissue culture cells, Proc. Natl. Acad. Sci. USA, 81, 6466–6470 (1984).
Bauer et al., Growth of avian adeno–associated virus in chicken cells transfected with fowl adenovirus serotype 1 DNA, Journal of Virological Methods, 29, 335–340 (1990).
Bauer et al., Herpesviruses Provide Helper Functions for Avian Adeno–associated Parvovirus, J. Gen. Virol. 67, 181–185 (1986).
Georg–Fries et al., Analysis of Proteins, Helper Dependence, and Seroepidemiology of a New Human Parvovirus, Virology 134, 61–71 (1984).
Schlehofer et al., Vaccinia Virus, Herpes Simplex Virus, and Carcinogens Induce DNA Amplification in a Human Cell Line and Support Replication of a Helpervirus Dependent Parvovirus, Virology 152, 110–117 (1986).
Flotte et al., Adeno–Associated Virus Vectors for In Vivo Gene Transfer, Journal of Cellular Biochemistry, Supp. 18A, 214 (1994).

Primary Examiner—Ponnathapura Achutamurthy
Assistant Examiner—Phuong T. Bui

[57] ABSTRACT

A novel method for preparing vectors derived from adeno-associated viruses (AAV), cells used therefor, and the use of the resulting vectors, particularly in gene and/or cell therapy, are disclosed.

26 Claims, 3 Drawing Sheets

METHOD FOR PREPARING RECOMBINANT ADENO-ASSOCIATED VIRUSES (AAV), AND USES THEREOF

The present invention relates to a novel method for preparing vectors derived from adeno-associated viruses (AAVs) and to the cells used for this purpose. More specifically, the present invention relates to a process for preparing recombinant AAVs using an animal helper virus. The invention also relates to the use of the recombinant AAVs obtained, particularly for gene and/or cellular therapy.

Gene therapy consists of correcting a deficiency or an abnormality (mutation, aberrant expression, etc.), or of ensuring the expression of a protein of therapeutic interest, by introducing genetic information into the cell or organ concerned. This genetic information can be introduced either in vitro into a cell extracted from the organ, with the modified cell then being reintroduced into the organism, or directly in vivo into the appropriate tissue. Various techniques have been described for transferring this genetic information, including diverse transfection techniques involving complexes of DNA and DEAE dextran (Pagano et al., J. Virol. 1 (1967) 891), of DNA and nuclear proteins (Kaneda et al., Science 243 (1989) 375), of DNA and lipids (Felgner et al., PNAS 84 (1987) 7413), and of DNA and polylysine, the use of liposomes (Fraley et al., J. Biol. Chem. 255 (1980) 10431), etc. More recently, the use of viruses as vectors for transferring genes has appeared as a promising alternative to these physicochemical transfection techniques. In this respect, a variety of viruses have been tested for their ability to infect certain cellular populations; in particular, retroviruses (RSV, HMS, MMS, etc.), HSV virus, the adenoviruses and the adeno-associated viruses.

Among these viruses, the adeno-associated viruses (AAV denoting "adeno-associated virus") offer certain properties which are attractive as regards utilization for transferring genes. The AAVs are DNA viruses of relatively small size which integrate, in a stable and site-specific manner, into the genome of the cells they infect. They are able to infect a wide spectrum of cells without having any effects on cell growth, on cell morphology or on cellular differentiation. Moreover, they do not seem to be involved in human disease.

The genome of the AAVs has been cloned, sequenced and characterized. It comprises about 4,700 bases and contains, at each end, an inverted repeat region (ITR) of approximately 145 bases, serving as the origin of replication of the virus. The remainder of the genome is divided into 2 essential regions carrying the encapsidation functions: the left-hand part of the genome, containing the rep gene involved in replication of the virus and expression of the viral genes and; the right-hand part of the genome, containing the cap gene encoding the capsid proteins of the virus. The use of vectors derived from AAVs for transferring genes in vitro and in vivo has been described in the literature (see, particularly, WO 91/18088; WO 93/09239; U.S. Pat. No. 4,797,368, U.S. Pat. No. 5,139,941, EP 488 528). These applications describe different constructs derived from the AAVs, in which constructs the rep and/or cap genes are deleted and replaced by a gene of interest, and their use for transferring the said gene of interest in vitro (to cells in culture) or in vivo (directly into an organism).

Nevertheless, the therapeutic use of the AAVs as vectors for transferring genes is currently limited, particularly because of the risks of contaminating the recombinant AAVs with a wild-type helper virus, and of using potentially tumorigenic human cell lines for producing the recombinant viruses. In order to replicate, the AAVs require the presence of a helper virus. The term helper virus denotes any virus which is able to supply in trans the functions which are required for replicating the AAVs. This can, in particular, be an adenovirus, a herpes virus or a vaccinia virus. In the absence of a helper virus of this nature, the AAVs remain in latent form in the genome of the infected cells but are not able to replicate and thus to produce viral particles. In general, therefore, the recombinant AAVs are produced by cotransfection, in a cell line infected with a human helper virus (for example an adenovirus), with a plasmid containing the gene of interest flanked by two AAV inverted repeat regions (ITR) and with a plasmid carrying the AAV encapsidation genes (rep and cap genes). The recombinant AAVs which are produced are then purified using conventional techniques. However, the AAVs obtained in this way are in general contaminated by the wild-type helper virus, which is also produced by the producer cell. The presence of this helper virus can have very adverse consequences in vivo such as, for example, a pathogenic or immunogenic effect. This helper virus can also be responsible for recombination events or else induce replication of the recombinant AAV and hence its transmission and dissemination.

The present invention provides an advantageous solution to this problem. The applicant has in effect developed a process for producing recombinant AAVs which makes it possible to produce stocks of recombinant AAVs which do not contain wild-type human helper virus. The process of the invention also makes it possible to avoid using potentially tumorigenic producer cells. The process of the invention is partly based on the demonstration that the recombinant AAVs can be produced by using a helper virus of animal origin. The applicant has in effect demonstrated that, surprisingly, a virus of animal origin was able to transcomplement a human AAV and, for this reason, it was possible to use this virus as a helper virus for producing human recombinant AAVs. This result is particularly advantageous since the animal virus used as helper virus cannot propagate in human cells and since no human pathology has been observed following infection with an animal helper virus. For this reason, even if the recombinant AAV preparations which are obtained may be contaminated by helper virus, the latter will not be able to cause any undesirable side effect in vivo. Furthermore, the process of the invention makes it possible to use animal producer cell lines which do not have any known tumorigenic effects on the human lines which are currently available. The invention is also based on the development of cell lines and of helper viruses which are particularly advantageous for producing recombinant AAVs.

A primary subject of the invention is thus a process for producing recombinant AAVs, according to which process the production is effected in the presence of an animal helper virus.

More preferably, the production is effected in an animal cell line infected with an animal helper virus.

The invention also relates, in a general manner, to the use of an animal helper virus for preparing recombinant AAVs.

As indicated above, the term helper virus denotes, within the meaning of the present invention, any virus which is capable of supplying in trans the functions which are required for replicating the AAVs. The helper virus which can be used in the process of the invention can be a virus of canine, bovine, murine, ovine, porcine, avian or even simian origin. It is preferably selected from among the adenoviruses, the herpes viruses or the vaccinia viruses.

Within the scope of the present invention, it is particularly advantageous to use an adenovirus of animal origin.

The adenoviruses of animal origin which can be used within the scope of the present invention can be of diverse origin, in particular of canine, bovine, murine (for example: Mav1, Beard et al., Virology 75 (1990) 81), ovine, porcine, avian or even simian (for example: SAV) origin.

More specifically, it is possible to cite, among the avian adenoviruses, serotypes 1 to 10 which are available from the ATCC, such as, for example, the Phelps (ATCC VR-432), Fontes (ATCC VR-280), P7-A (ATCC VR-827), IBH-2A (ATCC VR-828), J2-A (ATCC VR-829), T8-A (ATCC VR-830), and K-11 (ATCC VR-921) strains, or else the strains designated as ATCC VR-831 to 835.

Among the bovine adenoviruses, the various known serotypes can be used, particularly those available from the ATCC (types 1 to 8) under reference numbers ATCC VR-313, 314, 639–642, 768 and 769.

It is also possible to use the murine adenoviruses FL (ATCC VR-550) and E20308 (ATCC VR-528), the type 5 (ATCC VR-1343) or type 6 (ATCC VR-1340) ovine adenoviruses, the porcine adenovirus (5359) or the simian adenoviruses such as, in particular, the adenoviruses with the ATCC reference numbers VR-591–594, 941–943, 195–203, etc.

Preferably, adenoviruses of canine origin are used as helper virus within the scope of the present invention and, more preferably, use is made of all the strains of the CAV1 and CAV2 adenoviruses [for example, Manhattan strain or A26/61 (ATCC VR-800) strain]. The canine adenoviruses have been the subject of numerous structural studies. As a consequence, the complete restriction maps of the CAV1 and CAV2 adenoviruses have been described in the prior art (Spibey et al., J. Gen. Virol. 70 (1989) 165), and the E1a and E3 genes, as well as the ITR sequences, have been cloned and sequenced (see, in particular, Spibey et al., Virus Res. 14 (1989) 241; Linné, Virus Res. 23 (1992) 119, WO 91/11525). As the examples below demonstrate, the canine adenoviruses are highly efficient in transcomplementing the AAVs so that they can replicate.

These different viruses of animal origin can be obtained, for example, from strains deposited in collections, then amplified in competent cell lines and modified as required. Techniques for producing, isolating and modifying adenoviruses or herpes viruses have been described in the literature and may be used within the scope of the present invention [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO 91/18088, WO 90/09441, WO 88/10311, WO 91/11525]. These different viruses can then be modified, for example, by deletion, substitution, addition, etc. In particular, these viruses can, in certain cases, be modified so that they become defective in their replication.

As indicated above, the production of the recombinant AAVs according to the process of the present invention is preferably effected in an animal cell line which is infected with the helper virus.

In general, the cell line and the helper virus which is used are from the same species. In this respect, various animal cell lines which may be used within the scope of the present invention have been described in the literature. Thus, among the canine lines, the greyhound kidney cell line GHK (Flow laboratories) or the MDCK cell line (ATCC no. CRL6253) may be cited with advantage. The conditions for culturing these cells, and for preparing the viruses or the viral DNA, have been described in the literature (see, in particular, Macartney et al., Science 44 (1988) 9; Fowlkes et al., J. Mol. Biol. 132 (1979) 163). Other animal lines (available, for example, in collections) may also be used.

Advantageously, the process of the invention employs a canine cell line which is infected with a canine adenovirus.

More preferably, the process of the invention is implemented with, as the canine cell line, the MDCK or GHK line or a derivative of these lines. A derived line is understood to mean any line which is obtained from these lines and retains their ability to produce recombinant AAVs when cultivated, infected, and/or transfected in appropriate conditions. Derived lines can, in particular, be obtained by inserting exogenous genes, by mutagenesis, and/or by selecting subclones, as necessary.

In a preferred embodiment of the invention, the cell line which is used also possesses the AAV encapsidation functions.

As indicated above, the recombinant AAVs are generally produced by cotransfecting, in a cell line infected with a helper virus, with a plasmid containing the gene of interest flanked by two AAV inverted repeat regions (ITR) and with a plasmid carrying the AAV encapsidation functions. The fact that the encapsidation functions are deleted from the recombinant AAV and are supplied in trans on a plasmid makes it possible in effect to prepare recombinant AAVs which are defective, that is incapable, after having infected a target cell, of producing infectious viral particles. The AAV encapsidation functions essentially consist of the rep and cap genes or of any functional homologous gene. The rep gene is involved in viral replication as well as in expression of the viral genes, and the cap gene encodes the envelope proteins of the virus (VP1, VP2 and VP3). These genes have been characterized and their sequences have been described in the literature (Srivastava et al., J. Virol. 45 (1983) 555). A functional homologous gene is any gene which is obtained by modification (mutation, suppression, addition, etc.) of the rep or cap genes and which displays an activity of the same nature. Such functional homologous genes may equally well be genes obtained by hybridization from nucleic acid banks using probes which correspond to the rep or cap genes.

In order to make it possible to produce defective recombinant AAVs, the cell line therefore advantageously possesses, according to the invention, the AAV encapsidation functions. More preferably, the cell line which is used possesses one or more copies of the AAV rep and cap genes, or of functional homologous genes.

According to the present invention, the AAV encapsidation functions can be supplied by an encapsidation plasmid and/or by the animal helper virus which is used and/or be integrated into the genome of the cell line.

In a special embodiment of the invention, all the encapsidation functions are supplied by a plasmid termed the encapsidation plasmid. In this case, the process of the invention advantageously comprises cotransfecting an animal cell line which is infected with an animal helper virus with a vector carrying a gene of interest and at least one AAV ITR and with the said AAV encapsidation plasmid. More preferably, the AAV encapsidation plasmid carries at least the AAV rep and cap genes or functional homologues.

In another particularly advantageous embodiment of the invention, the encapsidation functions are supplied by the animal helper virus which is used and/or are integrated in the genome of the cell line. In this case, the process of the invention comprises transfecting a vector carrying a gene of interest and at least one AAV ITR into a cell line which is infected with an animal helper virus and which contains the encapsidation functions (integrated into the genome and/or carried by the helper virus). This embodiment is particularly advantageous since an encapsidation plasmid does not have to be used.

More preferably, in the process of the invention, the AAV rep gene, or a functional homologue of this gene, is integrated into the genome of the cell line and the AAV cap gene, or a functional homologue of this gene is carried by the animal helper virus. In another preferred variant of the implementation of the invention, a cell line is used which includes, inserted into its genome, the AAV rep and cap genes or functional homologous genes. In this preferred embodiment, the AAV rep and cap genes, or their functional homologues, may be introduced on a single construct or, sequentially, on separate constructs. In these different embodiments, the encapsidation functions can be placed under the control of their own promoter, of heterologous promoters or of artificial promoters. Advantageously, the encapsidation functions are placed under the control of inducible transcription regulation elements, making it possible to induce or suppress expression of the encapsidation functions according to the conditions. In a particularly advantageous embodiment, the AAV rep gene, or a functional homologous gene, is placed, in the constructs of the invention, under the control of an inducible promoter.

In still another preferred variant of the implementation of the invention, a helper virus is used which includes the AAV rep and cap genes, or functional homologous genes, in its genome.

The applicant has in effect demonstrated that it is possible to insert the encapsidation functions, or certain of them, directly into the genome of the helper virus which is used. In the same way, the applicant has also demonstrated that it is possible to insert the encapsidation functions, or certain of them, directly, in a stable manner, into the genome of the cell line which is used.

In this respect, a subject of the invention is also any animal cell line which can be infected by a helper virus in order to produce recombinant AAVs and which contains all or part of the AAV encapsidation functions integrated into its genome. Preferably, the invention relates to any animal cell line which includes the AAV rep gene, or a functional homologous gene, integrated into its genome. In another preferred embodiment, the invention relates to any animal cell line which includes the AAV rep and cap genes, or functional homologous genes, integrated into its genome.

The cell line is particularly advantageously a canine cell line, such as a line which is obtained, for example, from the MDCK or GHK lines.

The cell lines of the invention can be obtained by transfecting with a DNA fragment carrying the AAV encapsidation function(s) under the control of expression signals. The transfection may be effected by any technique which is known to the person skilled in the art (calcium phosphate precipitation, lipofection, electroporation, use of liposomes, etc.). Preferably, the transfection is effected in the presence of calcium phosphate (see example 5). Various expression signals may be used for controlling the expression of the encapsidation functions. These expression signals can be, in particular, the native promoters of the rep or cap genes, heterologous promoters or even synthetic promoters. In one particularly advantageous embodiment, the AAV encapsidation functions are placed, in the cell lines according to the invention, under the control of inducible promoters (LTR-MMTV, Tc, etc.). Employment of promoters of this type is particularly advantageous since this makes it possible to modulate the effect of the rep gene, especially on the helper virus which is used. A subject of the invention is thus also any cell line which can be infected by a helper virus for the purpose of producing recombinant AAVs and which includes all or part of the AAV encapsidation functions integrated into its genome under the control of one or more inducible promoters.

In the case of a line which includes the AAV rep and cap genes (or functional homologues), these genes may be transfected either on a single construct or, in a sequential manner, on two separate constructs. This second method of preparation is particularly advantageous since it limits the recombination events as far as possible. The lines which are obtained in this way are therefore particularly stable. Furthermore, the construct which is used for the transfection advantageously also carries a gene which makes it possible to select the transformed cells, and for example the gene for resistance to geneticin. The resistance gene may also be carried by a different DNA fragment which is cotransfected with the first fragment.

After transfection, the tranformed cells are selected (for example on the basis of their resistance to geneticin) and their DNA is analysed by Northern blotting in order to confirm integration of the DNA fragment or fragments (when 2 separate constructs are used) into the genome. The ability of the resulting cells to encapsidate the AAVs may then be tested by infecting with a recombinant AAV which lacks the said functions.

A subject of the invention is also any helper virus for producing recombinant AAVs which includes, inserted into its genome, all or part of the AAV encapsidation functions. More preferably, the invention relates to any helper virus for producing recombinant AAVs which includes, inserted into its genome, the AAV rep gene or a functional homologous gene. Also preferably, the invention relates to any helper virus for producing recombinant AAVs which includes, inserted into its genome, the AAV rep and cap genes or functional homologous genes.

Advantageously, the helper virus for producing recombinant AAVs is an adenovirus. The adenoviruses which include the AAV encapsidation functions according to the invention can be prepared by homologous recombination between an adenovirus and a plasmid which carries, inter alia, the said encapsidation functions. The homologous recombination takes place following cotransfection of the said adenovirus and plasmid into an appropriate cell line. As an example of a line, mention may be made of the human embryonic kidney line 293 (Graham et al., J. Gen. Virol. 36 (1977) 59) which contains, in particular, integrated into its genome, the left-hand part of the genome of an Ad5 adenovirus (12%), or of the MDCK line. Subsequently, the replicated vectors are recovered and purified by the conventional techniques of molecular biology.

Still more particularly, the adenovirus is an adenovirus of human origin, preferably selected from the Ad2 and Ad5 adenoviruses; or of animal origin, preferably selected from the canine adenoviruses (CAV1 and CAV2). The AAV encapsidation functions may be introduced into different regions of the genome of the helper virus of the invention. Advantageously, the encapsidation funtions are inserted into a region such that the ability of the virus to transcomplement the AAVs is not disrupted. It is also possible to insert the encapsidation functions into a functional region of the genome of the helper virus, which region is then supplied in trans either by a plasmid or by the cell line which is used. Thus, as regards the human adenoviruses Ad2 or Ad5, it is possible, for example, to insert the rep gene, the cap gene or the rep and cap genes so that it/they replace(s) the E1 gene. The resulting adenovirus can be used as the helper virus for producing recombinant AAVs in the cell line 293, which carries the E1 gene in its genome (see Example 6).

The process of the invention thus makes it possible to produce recombinant AAVs which can be used therapeutically. The recombinant AAVs which are obtained can be any AAV whose genome at least has been modified by inserting a gene of interest. As pointed out above, various types of recombinant AAVs have been described in the prior art (WO 91/18088; WO 93/09239; U.S. Pat. No. 4,797,368, U.S. Pat. No. 5,139,941, EP 488 528). In general, these AAVs include partial or total deletions in the rep and/or cap genes, at which deletions a gene of interest is inserted. These recombinant AAVs can be prepared from different AAV serotypes such as AAV1, AAV2, AAV3 and AAV4 and, preferably, from AAV2 strains. The gene of interest can, in particular, be a therapeutic gene.

Within the meaning of the invention, a therapeutic gene is understood, especially, to mean any gene which encodes a proteinaceous product possessing a therapeutic effect. The proteinaceous product encoded in this way can be a protein, a peptide, etc. This proteinaceous product can be homologous in relation to the target cell (i.e. a product which is normally expressed in the target cell when the latter is not displaying any pathology). In this case, the expression of a protein makes it possible, for example, to compensate for insufficient expression in the cell or for the expression of a protein which is inactive or weakly active due to having been modified, or even to overexpress the said protein. The therapeutic gene can also encode a mutant of a cellular protein, which mutant possesses enhanced stability, a modified activity, etc. The proteinaceous product can also be heterologous in relation to the target cell. In this case, an expressed protein can, for example, complement or supply a deficient activity in the cell, allowing the latter to resist a pathological process, or else stimulate an immune response.

The therapeutic products which may be cited within the meaning of the present invention include, more especially, enzymes, blood products, hormones, lymphokines: interleukins, interferons, TNF, etc. (FR 9203120), growth factors (erythropoietin, G-CSF, M-CSF, GM-CSF, etc.) neurotransmitters or their precursors or enzymes responsible for synthesizing them, the trophic factors: BDNF, CNTF, NGF, IGF, GMF, aFGF, bFGF, NT3, NT5, HARP/pleiotrophin, etc.; the apolipoproteins; ApoAI, ApoAIV, ApoE, etc. (FR 93 05125), lipoprotein lipase (LPL), dystrophin or a minidystrophin (FR 9111947), the CFTR protein associated with cystic fibrosis, the tumour-suppressing genes: p53, Rb, Rap1A, DCC, k-rev, etc. (FR 93 04745), genes encoding the following factors involved in coagulation: Factors VII, VIII, IX, genes intervening in the repair of DNA, suicide genes (thymidine kinase or cytosine deaminase), etc.

The therapeutic gene can also be an antisense gene or sequence whose expression in the target cell makes it possible to control the expression of genes or the transcription of cellular mRNAs. Such sequences can, for example, be transcribed in the target cell into RNAs which are complementary to cellular mRNAs and thus block translation of the latter into protein, in accordance with the technique described in patent EP 140 308. The antisense sequences also include sequences encoding ribozymes which are able to destroy target RNAs selectively (EP 321 201).

The gene of interest can also contain one or more sequences encoding an antigenic peptide which is able to generate an immune response in man or animals. In this particular embodiment of the invention, the recombinant AAVs can be used for producing vaccines or immunotherapeutic treatments which are applied to man or animals, especially against microorganisms, viruses or cancers. These vaccines or immunotherapeutic treatments can, in particular, be antigenic peptides which are specific for the Epstein Barr virus, the HIV virus, the hepatitis B virus (EP 185 573), the pseudorabies virus, or else specific for tumours (EP 259 212).

Preferably, the gene of interest also includes sequences permitting its expression in the desired cell or organ. These can be sequences which are naturally responsible for expressing the gene in question when they are capable of functioning in the infected cell. They can also be sequences having a different origin (sequences which are responsible for expressing other proteins or even synthetic sequences). In particular, they can be promoter sequences of eukaryotic or viral genes. For example, they can be promoter sequences stemming from the genome of the cell which is to be infected. Likewise, they can be promoter sequences stemming from the genome of a virus. In this respect, the promoters of the genes E1A, MLP, CMV, LTR-RSV, etc., may be cited by way of example. Furthermore, these expression sequences can be modified by adding activation sequences, regulatory sequences or sequences which confer tissue-specific expression on the gene of interest.

In addition, the gene of interest can also include a signal sequence which directs the synthesized therapeutic product into the secretory pathways of the target cell. This signal sequence can be the natural signal sequence of the therapeutic product, but can also be any other functional signal sequence or else an artificial signal sequence.

The recombinant AAVs prepared in accordance with the present invention can be used for transferring genes of interest in vitro, ex vivo or in vivo. In vitro, they can make it possible to transfer a gene to a cell line, for example for the purpose of producing a recombinant protein. Ex vivo, they can be used for transferring a gene to a population of cells which has been removed from an organism, and, where appropriate, selected and amplified, with the aim of conferring desired properties on these cells with a view to readministering the cells to an organism. In vivo, they can be used for transferring genes by directly administering a solution which is purified and, where appropriate, combined with one or more pharmaceutical excipients. In this latter case, the recombinant AAVs can be formulated for the purpose of administering them by the topical, cutaneous, oral, rectal, vaginal, parenteral, intranasal, intravenous, intramuscular, subcutaneous, intraocular, transdermal, etc., route. Preferably, they are combined with a pharmaceutical excipient which is acceptable for an injectable formulation, especially for injection directly into the desired organ. These formulations can, in particular, be sterile or isotonic solutions, or dry, especially lyophilized, compositions which allow the constitution of injectable solutions by the addition of, as the case may be, sterilized water or physiological serum. The doses of AAVs used for the injection, as well as the number of administrations, can be adapted according to different parameters, especially according to the mode of administration used, the pathology concerned, the gene to be expressed, or else the sought-after duration of the treatment.

The present invention thus provides a particularly advantageous method for preparing recombinant AAVs which can be used therapeutically, especially in a method for treating diseases, comprising the administration in vivo of a recombinant AAV which contains a gene which is capable of remedying the said disease. More particularly, this method is applicable to diseases resulting from a deficiency in a proteinaceous or nucleic product, with the gene of interest encoding the said proteinaceous product or containing the said nucleic product.

The present invention will be described in more detail with the aid of the following examples, which are to be considered as being illustrative and not delimiting.

GENERAL TECHNIQUES OF MOLECULAR BIOLOGY

The methods conventionally used in molecular biology, such as preparative extractions of plasmid DNA, centrifugation of plasmid DNA in a caesium chloride gradient, electrophoresis on agarose or acrylamide gels, purification of DNA fragments by electroelution, extraction of proteins with phenol or phenol/chloroform, precipitation of DNA in a saline medium using ethanol or isopropanol, transformation into Escherichia coli, etc., are well known to the person skilled in the art and are abundantly described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The plasmids of the pBR322 and pUC type, and the phages of the M13 series, were obtained commercially (Bethesda Research Laboratories).

For the ligations, the DNA fragments can be separated according to their size by electrophoresis on agarose or acrylamide gels, extracted with phenol or with a phenol/chloroform mixture, precipitated using ethanol and then incubated in the presence of phage T4 DNA ligase (Biolabs) in accordance with the supplier's recommendations.

The protruding 5' ends can be filled in using the Klenow fragment of *E. coli* DNA polymerase I (Biolabs) according to the supplier's specifications. The protruding 3' ends are removed in the presence of phage T4 DNA polymerase (Biolabs), used in accordance with the manufacturer's recommendations. The protruding 5' ends are removed by careful treatment with S1 nuclease.

In vitro site-directed mutagenesis using synthetic oligodeoxynucleotides can be carried out in accordance with the method developed by Taylor et al. [Nucleic Acids Res. 13 (1985) 8749–8764] using the kit supplied by Amersham.

Enzymic amplification of DNA fragments by the technique termed PCR [polymerase-catalyzed chain reaction, Saiki R. K. et al., Science 230 (1985) 1350–1354; Mullis K. B. and Faloona F. A., Meth. Enzym. 155 (1987) 335–350 can be carried out using a DNA thermal cycler (Perkin Elmer Cetus) in accordance with the manufacturer's specifications.

The nucleotide sequences can be verified by the method developed by Sanger et al. [Proc. Natl. Acad. Sci. USA, 74 (1977) 5463–5467] using the kit supplied by Amersham.

EXAMPLE 1

Construction of the encapsidation plasmid pREP-CAP

This example describes the construction of a plasmid, termed encapsidation plasmid, which carries the necessary functions for encapsidating a recombinant AAV. More precisely, this plasmid, designated pREP-CAP, carries the rep and cap genes of AAV2.

Figure 1:
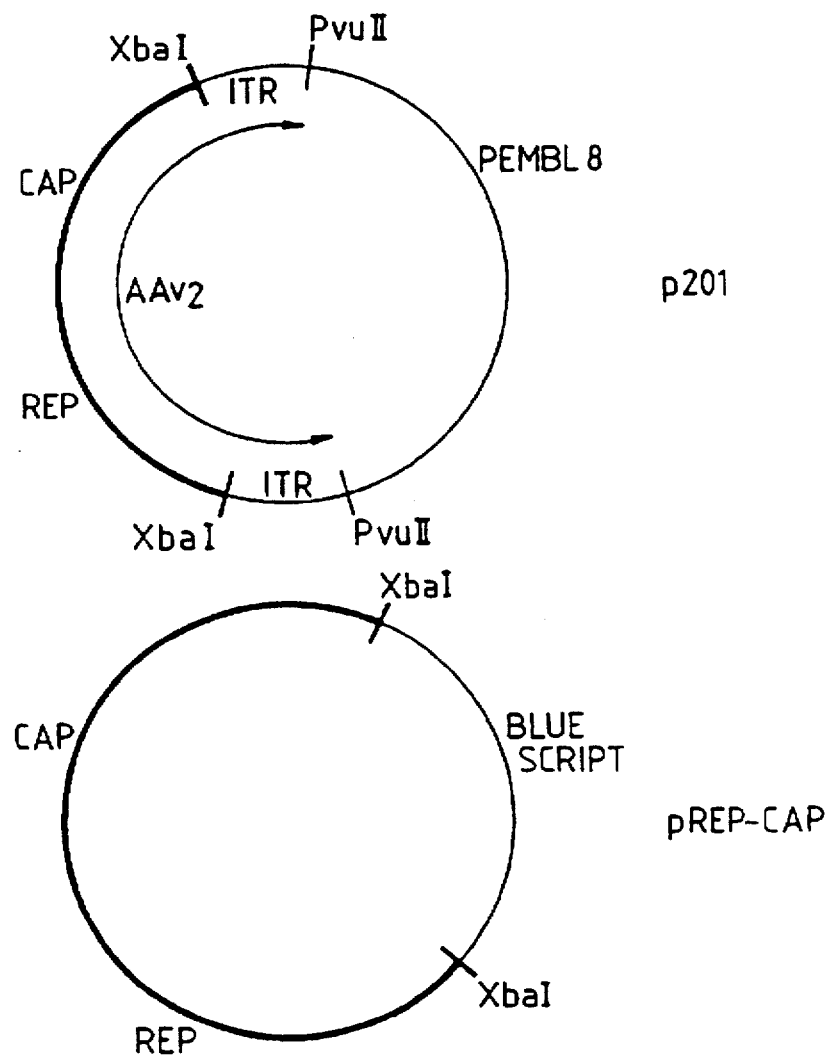
FIG. 1: Representation of the plasmid pREP-CAP

The plasmid pREP-CAP was constructed in the following manner: the AAV2 genome, whose ITRs had been deleted, was isolated from the plasmid p201 by digesting with the enzyme XbaI. The plasmid p201 contains the entire AAV2 genome cloned in the PvuII site of the plasmid pEMBL8 (Samuiski et al., J. Virol. 61 (1987) 3096). The fragment thus obtained, carrying the rep and cap genes, was then cloned into the XbaI site of the Bluescript plasmid (Stratagene). The structure of this plasmid is depicted in FIG. 1.

EXAMPLE 2

Construction of the AAV plasmid pAAV-EPO-NEO

Figure 2:
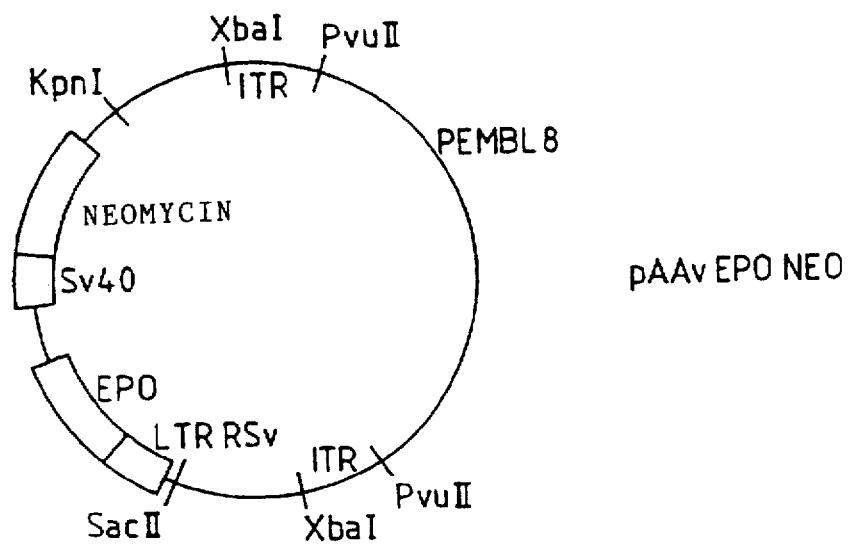
FIG. 2: Representation of the plasmid pAAV-EPO-NEO

This example describes the construction of an AAV plasmid which carries the cDNA encoding erythropoietin, a marker gene, and two AAV2 ITRs. This plasmid has been designated pAAV-EPO-NEO (FIG. 2).

In order to construct this plasmid, an expression cassette was prepared which contained the cDNA encoding erythropoietin (cynomolgus) under the control of the LTR of the Rous sarcoma virus (RSV), followed by the gene neo, conferring resistance to neomycin, under the control of the early promoter of the SV40 virus. This cassette was then inserted into the SacII/KpnI sites of the plasmid p201, replacing the corresponding fragment containing the rep and cap genes (FIG. 2).

EXAMPLE 3

Production of canine adenovirus CAV2 in the cell line MDCK

This example describes the production of canine adenovirus CAV2 in the canine cell line MDCK.

The MDCK cells were cultivated in a DMEM medium which was supplemented with 10% calf serum (see, in addition, Macartney et al., Science 44 (1988) 9 for the culture conditions). The confluent cells were then infected with a suspension of CAV2 virus (approximately 5 pfu/cell). At from 30 to 48 hours after infection, the infected cells were harvested and concentrated by centrifugation. The pellet which is obtained can be used to purify the CAV2 adenoviruses on caesium chloride. However, if the titres are too weak, the pellet is preferably subjected to a cycle of freezing and thawing and the resulting supernatant is then used to amplify the CAV2 viruses. For this, the supernatant is used to reinfect the MDCK cells, under the same conditions, and the protocol described above for recovering the viruses is then repeated. This procedure makes it possible to obtain a purified solution of CAV2 adenovirus which can be used as helper virus for producing recombinant AAVs.

EXAMPLE 4

Production of recombinant AAV carrying the erythropoietin gene in the MDCK cell line infected with a canine helper adenovirus This example describes the production of an AAV recombinant carrying the erythropoietin gene in the MDCK cell line infected with the canine adenovirus CAV2.

The MDCK cells (at 50% confluence) were infected with CAV2 adenovirus, prepared under the conditions of Example 3, at 5–10 pfu/cell. At from 4 to 6 hours after infection, the cells were cotransfected, by lipofection (Fegner et al., PNAS 84 (1987) 7413), with 5 μg of plasmid pAAV-EPO-NEO and 5 μg of plasmid pREP-CAP. At from 48 to 72 hours after this, the cells were harvested and subjected to several cycles of freezing and thawing. The resulting suspension was subsequently centrifuged (15 minutes at 4000 rpm) and the supernatant, containing the recombinant AAVs, was then recovered and heated at 56° C. for 30 minutes.

In order to establish the infectivity and erythropoietin expression, samples of the supernatant were used to infect Hela cells. The Hela cells are derived from a human epithelial carcinoma. This line can be obtained from the ATCC (ref. CCL2) as can the conditions for culturing it. The cells and the supernatant were harvested at 24 hours after infection. The presence of the AAV-EPO recombinant genome in these cells was subsequently confirmed by carrying out Southern blot hybridization experiments on the cellular DNA extracted by the Hirt technique (Gluzman and Van Doren, J. Virol. 45 (1983) 91). In addition, the presence of erythropoietin in the supernatant was demonstrated by a biological test.

These results clearly show that recombinant AAVs can be efficiently prepared in an animal system (cell line and helper virus).

EXAMPLE 5

Construction of cell lines containing the AAV encapsidation functions

This example describes the construction of cell lines containing all or part of the AAV encapsidation functions. These lines permit the construction of recombinant AAVs according to the invention from which these regions are deleted, without having to make use of an encapsidation plasmid. These viruses are obtained by in vivo recombination and can include extensive heterologous sequences.

The lines of the invention are constructed by transfecting appropriate cells with a DNA fragment which carries the indicated genes under the control of a transcriptional promoter and a terminator (polyadenylation site).

The transfection may be effected in different ways, especially in the presence of calcium phosphate, by lipofection, by electroporation, etc. In this example, the transfection is carried out in the presence of calcium phosphate.

The terminator can either be the natural terminator of the transfected gene or a different terminator, such as, for example, the terminator of the early messenger of the SV40 virus.

In the cell lines described, the rep and/or cap genes are placed under the control of an inducible promoter; the LTR of MMTV (Pharmacia), which is induced by dexamethasone. It is understood that other promoters can be used, especially variants of the LTR of MMTV carrying, for example, heterologous regulatory regions (especially the enhancer region), or else the tetracycline (Tc) promoter. Moreover, as indicated in the description, the promoter can also be the native promoter of the gene which is employed.

Advantageously, the DNA fragment also carries a gene permitting selection of the transformed cells. This gene can, in particular, be a gene for resistance to an antibiotic, such as, for example, the gene encoding resistance to geneticin. This marker gene can also be carried by a different DNA fragment which is cotransfected with the first fragment.

After transfection, the transformed cells are selected (resistance to geneticin) and their DNA is analysed by Northern blotting in order to confirm integration of the DNA fragment or fragments (when 2 separate constructs are used) into the genome. The cells are then tested for their ability to encapsidate the recombinant AAVs following infection with the appropriate helper virus and transfection with an appropriate AAV plasmid.

This technique renders it possible to obtain the following cell lines:

1. MDCK cells possessing the rep gene under the control of the LTR of MMTV;
2. MDCK cells possessing the rep and cap genes, on the same DNA fragment, under the control of the LTR of MMTV;
3. MDCK cells possessing the rep and cap genes, on two distinct DNA fragments, under the control of the LTR of MMTV.

EXAMPLE 6

Construction of an adenovirus containing the AAV encapsidation functions

This example describes the construction of an adenovirus containing the AAV rep and cap genes inserted into its genome. The adenovirus Ad-RSV.Rep-Cap was obtained by in vivo homologous recombination between the mutant adenovirus Ad.dl1324 (Thimmappaya et al., Cell 31 (1982) 543] and the vector pAd.RSV.Rep-Cap.

Figure 3:
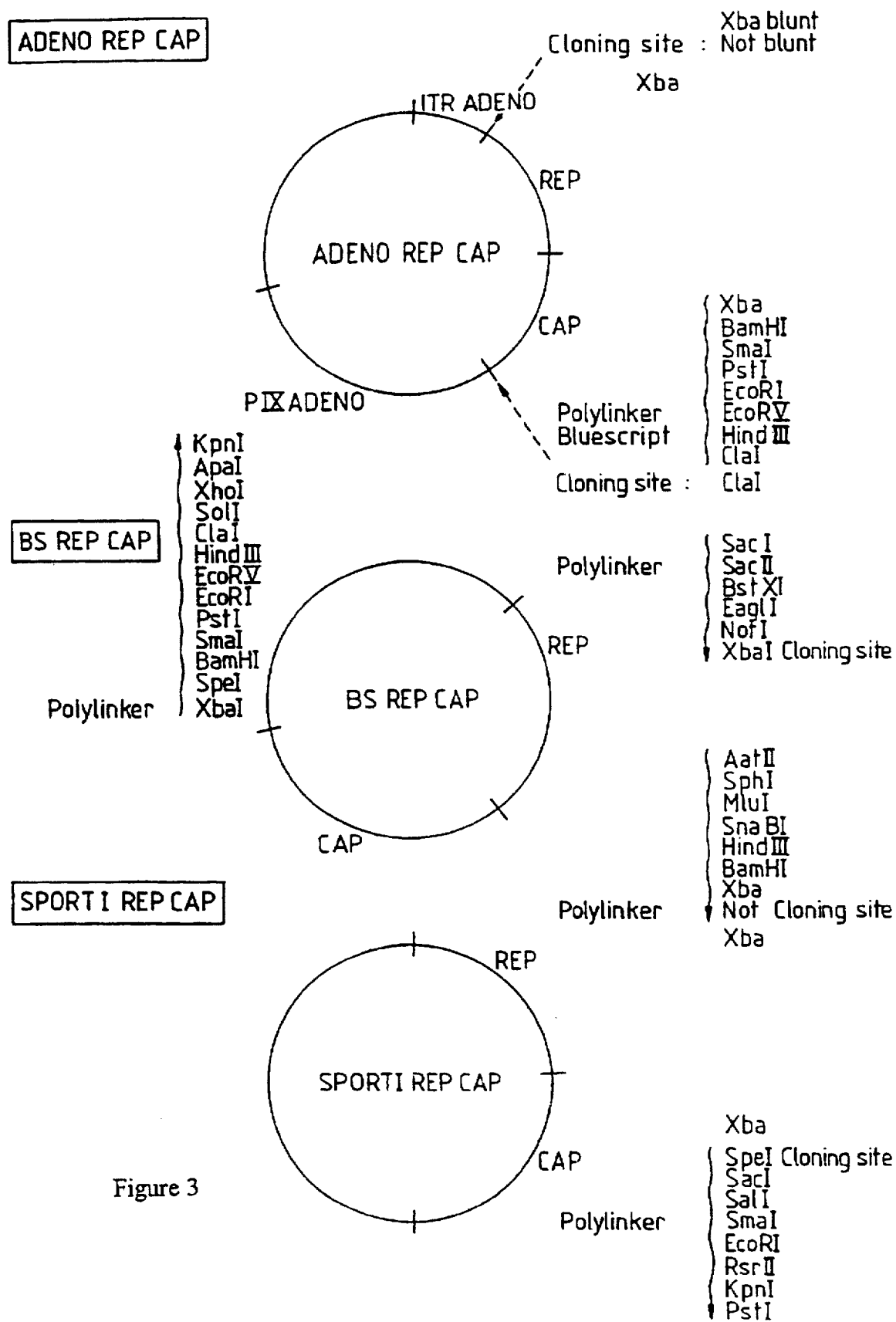
FIG. 3: Representation of the plasmid pAd-RepCap

6.1 Construction of the plasmid pAd.RSV.Rep-Cap (FIG. 3)

The plasmid pAd.RSV.Rep-Cap was constructed from the plasmid pAd.RSV.βGal [Stratford-Perricaudet et al., J. Clin. Invest. (1992) 626] by substituting a DNA fragment carrying the AAV rep and cap genes for the β-gal gene.

In order to do this, the XbaI fragment containing the AAV2 genome, whose ITRs had been deleted, was isolated from the plasmid p201 (cf. Example 1). This fragment was then subcloned into the XbaI site of the Bluescript plasmid. This step then renders it possible to isolate the fragment encompassing the AAV rep and cap genes in the form of a NotI/ClaI fragment. This fragment was then cloned into the XbaI (situated downstream of the left-hand ITR) and ClaI (situated upstream of PIX of the Ad5) sites of the vector pAd.RSV.βGal, resulting in the substitution of the βgal gene by the rep and cap genes.

6.2 Construction of the defective recombinant adenovirus Ad.RSV.Rep-Cap

The plasmid pAd.RSV.Rep-Cap and the adenovirus Ad.dl1324, linearized with the enzyme ClaI, are cotransfected into the line 293 in the presence of calcium phosphate in order to enable homologous recombination to take place. The recombinant adenoviruses which are generated in this way are selected by plaque purification. Following isolation, the DNA of the recombinant adenovirus is amplified in cell line 293.

In general, the viral particles are purified by centrifugation on a caesium chloride gradient in accordance with known techniques (see, in particular, Graham et al., Virology 52 (1973) 456). The Ad.RSV.Rep-963 Cap adenovirus can be preserved in 20% glycerol at −80° C.

The same strategy can be repeated while inserting only one of the rep or cap genes. Moreover, the insertion can be carried out at different sites in the adenovirus genome.

We claim:

1. A process for producing recombinant human adeno-associated viruses (AAVs), comprising transfecting a cell line infected with an animal helper virus that cannot propagate in human cells with a plasmid containing a gene of interest flanked by two AAV inverted repeats (ITRs), wherein the helper virus is selected from the group consisting of adenovirus, herpes virus, and vaccinia virus, wherein AAV encapsidation function genes have been deleted from the plasmid, and wherein the cell line expresses the AAV encapsidation function genes; and obtaining the recombinant human AAV.

2. The process according to claim 1, wherein the cell line is an animal cell line infected with an animal helper virus.

3. The process according to claim 1, wherein the animal helper virus is a virus of canine, bovine, murine, ovine, porcine, avian or simian origin.

4. The process according to claim 1, wherein the animal helper virus is selected from among the adenoviruses, the herpes viruses and the vaccinia viruses.

5. The process according to claim 4, wherein the animal helper virus is an adenovirus.

6. The process according to claim 5, wherein the animal helper virus is a canine adenovirus.

7. The process according to claim 6, wherein the animal helper virus is selected from among the CAV-1 and CAV-2 strains.

8. The process according to claim 6, wherein the cell line is a canine cell line.

9. The process according to claim 8, wherein the cell line is a Madin-Darby canine kidney (MDCK) line or a greyhound kidney (GHK) line.

10. The process according to claim 2, wherein the AAV encapsidation function genes are supplied by an encapsidation plasmid, or by the animal helper virus, or by integration into the genome of the cell line.

11. The process according to claim 10, wherein the AAV encapsidation functions consist of the AAV rep and cap genes, placed under the control of heterologous transcription regulation elements.

12. The process according to claim 11, wherein the AAV rep gene is integrated into the genome of the line, and the AAV cap gene is carried by the animal helper virus.

13. The process according to claim 11, wherein the AAV rep and cap gene are integrated into the genome of the cell line.

14. The process according to claim 11, wherein the AAV rep and cap genes are carried by the helper virus.

15. A cell line which comprises human AAV encapsidation function genes integrated into its genome, wherein the cell line is an animal cell line, and wherein the cell line has been infected with an animal helper virus that cannot propagate in human cells, wherein the helper virus is selected from the group consisting of adenovirus, herpes virus, and vaccinia virus.

16. The animal cell line of claim 15, wherein one or more of the encapsidation function genes are under the control of an inducible promoter.

17. The cell line according to claim 15, comprising a human AAV rep gene integrated into its genome.

18. The cell line according to claim 15, comprising human AAV rep and cap genes integrated into its genome.

19. The cell line according to claim 15, wherein the inducible promoter is selected from among the LTR of MMTV or the Tc promoter.

20. The cell line according to claim 15, obtained from MDCK or GHK lines.

21. An animal helper virus for producing recombinant human AAVs which includes, inserted into its genome, a human AAV encapsidation function gene, wherein the animal helper virus cannot propagate in human cells, and wherein the helper virus, is selected from the group consisting of adenovirus, herpes virus. and vaccinia virus.

22. The animal helper virus according to claim 21, which includes, inserted into its genome, the AAV rep gene.

23. The animal helper virus according to claim 21, which includes, inserted into its genome, the AAV rep and cap genes.

24. The animal helper virus according to claim 21, which is an adenovirus.

25. The animal helper virus according to claim 24, which is a canine adenovirus.

26. The animal helper virus according to claim 25 selected from among the CAV1 and CAV2 adenoviruses.

* * * * *